(12) United States Patent
Koster et al.

(10) Patent No.: US 7,624,617 B2
(45) Date of Patent: Dec. 1, 2009

(54) GAS ANALYZING SYSTEM, LITHOGRAPHIC APPARATUS AND METHOD OF IMPROVING A SENSITIVITY OF A GAS ANALYZING SYSTEM

(75) Inventors: Norbertus Benedictus Koster, Delft (NL); Richard Versluis, Delft (NL); Bart Dinand Paarhuis, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 239 days.

(21) Appl. No.: 11/602,496

(22) Filed: Nov. 21, 2006

(65) Prior Publication Data

US 2008/0128636 A1    Jun. 5, 2008

(51) Int. Cl.
*G01N 7/00* (2006.01)
*G01N 37/00* (2006.01)
(52) U.S. Cl. ....................................... 73/23.2
(58) Field of Classification Search ............... 73/23.2; 250/492.1
See application file for complete search history.

(56) References Cited

U.S. PATENT DOCUMENTS

| | | | | |
|---|---|---|---|---|
| 5,037,516 A | * | 8/1991 | Buck | 204/192.15 |
| 5,504,328 A | * | 4/1996 | Bonser | 250/288 |
| 2002/0030801 A1 | * | 3/2002 | Endo et al. | 355/53 |
| 2004/0079136 A1 | * | 4/2004 | Pillion | 73/23.2 |
| 2004/0100623 A1 | * | 5/2004 | Bisschops | 355/53 |

FOREIGN PATENT DOCUMENTS

EP    1 223 468 A1    7/2002

OTHER PUBLICATIONS

Blessing et al., Recommended practice for process sampling for partial pressure analysis, *J. Vac. Sci. Technol.* A 25 (1), Jan./Feb. 2007, pp. 167-186.
International Search Report for Appln. No. PCT/NL2007/050545 mailed May 26, 2008, 3 pgs.
Allain et al., "Studies of liquid-metal erosion and free surface flowing liquid lithium retention of helium at the University of Illinois," Fusion Engineering and Design, 72: 1-3, Elsevier Science Publishers, Amsterdam, NL, Nov. 1, 2004, pp. 93-110.
Ganguly et al., "ABsense of a Steady State in Hydrogen Diluted Silane plasmas due to Mass Dependent Gas Pumping Speeds and its Consequences," Materials Research Society Symposium Proceedings, 715, 2002, pp. A1.4.1-A1.4.5.

* cited by examiner

*Primary Examiner*—Daniel S Larkin
(74) *Attorney, Agent, or Firm*—Sterne, Kessler, Goldstein & Fox P.L.L.C.

(57) ABSTRACT

A gas analyzing system is disclosed, the system including a gas analyzer and a reduced pressure chamber in which interior the gas analyzer is arranged, the reduced pressure chamber having an inlet configuration for a gas mixture inflow and an outlet configuration for a gas mixture outflow, wherein the outlet configuration during operation is connected to a pump system to facilitate the gas mixture outflow, the outlet configuration having a channel section and a flow section, the flow section having a cross-sectional area that is smaller than the cross-sectional area of the channel section.

7 Claims, 3 Drawing Sheets

GAS ANALYZING SYSTEM, LITHOGRAPHIC APPARATUS AND METHOD OF IMPROVING A SENSITIVITY OF A GAS ANALYZING SYSTEM

FIELD

The invention relates to a gas analyzing system, a lithographic apparatus and a method of improving a sensitivity of a gas analyzing system.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In lithography systems, contamination of gas with carbon hydroxyl particles originating from substrate structures might damage optical elements, such as mirrors. Particularly, extreme ultraviolet (EUV) lithography systems might suffer from such gas contamination. To help prevent damage, a lithography system may be provided with a gas analyzing system to detect gas contamination.

To measure the concentration of a contaminant in a gas mixture, a residual gas analyzer (RGA) is often used as the gas analyzer. At a pressure exceeding a working pressure of the RGA, the measurement may be performed by diluting the gas mixture, e.g. by flowing it through an orifice of an inlet configuration into a reduced pressure chamber, and by connecting the reduced pressure chamber via a channel section of an outlet configuration to a pump system. By employing a reliable calibration, a concentration down to 10 parts per billion (PPB) may be measured.

For contaminant measuring, the main gas component of the mixture, also called the carrier gas, is often of no interest. The partial pressure of the main gas component, however, substantially determines the operating pressure in the reduced pressure chamber and at the RGA. Further, the dynamic range of the RGA and/or the lowest detection level of the RGA determines the lowest level of contaminant that can be measured.

SUMMARY

When $H_2$ is the main gas component, the poor $H_2$ pumping speed of modern pumping systems—which is particle mass dependent—determines the total pressure in the reduced pressure chamber, while other gas species are pumped away at a higher pumping speed. This means that the species of interest is pumped faster than the carrier gas and that its partial pressure is even lower than in the original mixture. Consequently, the sensitivity of the system may deteriorate.

It is desirable, for example, to provide a gas analyzing system wherein the sensitivity is improved.

According to an aspect of the invention, there is provided a gas analyzing system, comprising:

a gas analyzer; and a reduced pressure chamber in which interior the gas analyzer is arranged, the reduced pressure chamber having an inlet configuration for a gas mixture inflow and an outlet configuration for a gas mixture outflow, wherein the outlet configuration during operation is connected to a pump system to facilitate the gas mixture outflow, the outlet configuration comprising a channel section and a flow section, the flow section having a cross-sectional area that is smaller than a cross-sectional area of the channel section.

According to an aspect of the invention, there is provided a gas analyzing system, comprising:

a gas analyzer; and a reduced pressure chamber in which interior the gas analyzer is arranged, the reduced pressure chamber having an inlet configuration for a gas mixture inflow and an outlet configuration for a gas mixture outflow, wherein the outlet configuration during operation is connected to a pump system to facilitate the gas mixture outflow, the outlet configuration comprising a channel section having a minimum cross-sectional area between about 80 $mm^2$ and about 2000 $mm^2$.

According to an aspect of the invention, there is provided a lithographic apparatus, comprising a support constructed to support a patterning device, the patterning device configured to impart a radiation beam with a pattern in its cross-section to form a patterned radiation beam; a substrate table constructed to hold a substrate; a projection system configured to project the patterned radiation beam onto a target portion of the substrate; a vacuum wall configured to keep a path of the radiation beam in vacuum; and a gas analyzing system as described herein.

According to an aspect of the invention, there is provided a method of improving a sensitivity of a gas analyzing system, comprising a gas analyzer and a reduced pressure chamber in which interior the gas analyzer is arranged, the reduced pressure chamber having an inlet configuration for a gas mixture inflow and an outlet configuration for a gas mixture outflow, wherein the outlet configuration during operation is connected to a pump system to facilitate the gas mixture outflow, the outlet configuration comprising a channel section, the method comprising providing the outlet configuration with a flow section having a cross-sectional area that is smaller than a cross-sectional area of the channel section.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
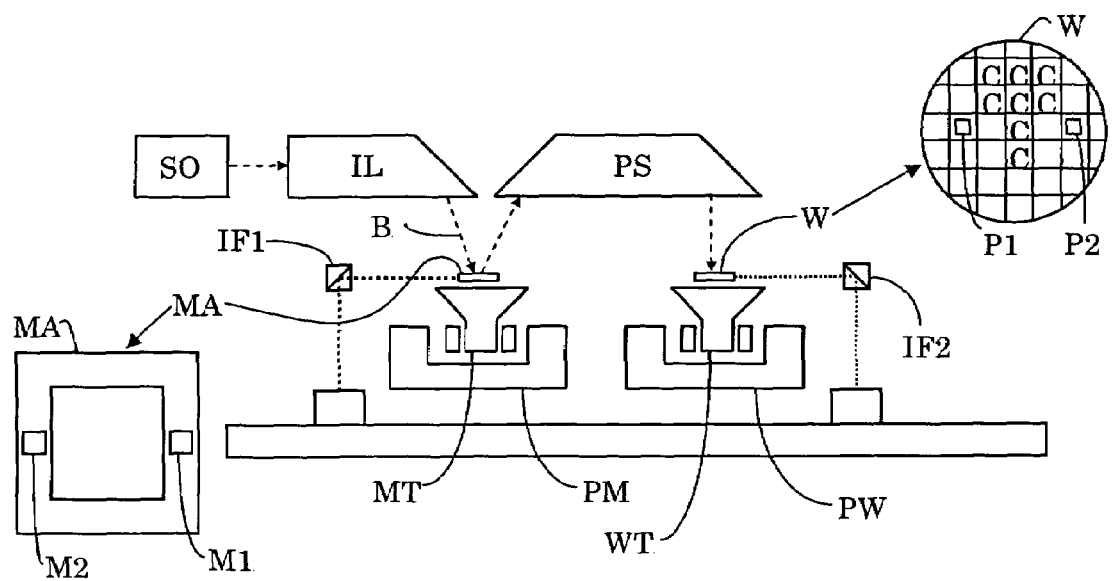
FIG. 1 depicts a lithographic apparatus according to an embodiment of the invention.

FIG. 1 schematically depicts a lithographic apparatus according to one embodiment of the invention. The apparatus comprises:

- an illumination system (illuminator) IL configured to condition a radiation beam B (e.g. UV radiation or other radiation);
- a support structure (e.g. a mask table) MT constructed to support a patterning device (e.g. a mask) MA and connected to a first positioner PM configured to accurately position the patterning device in accordance with certain parameters;
- a substrate table (e.g. a wafer table) WT constructed to hold a substrate (e.g. a resist-coated wafer) W and connected to a second positioner PW configured to accurately position the substrate in accordance with certain parameters;
- a projection system (e.g. a refractive projection lens system) PS configured to project a pattern imparted to the radiation beam B by patterning device MA onto a target portion C (e.g. comprising one or more dies) of the substrate W; and
- a vacuum wall configured to keep the path of the radiation beam in vacuum.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more support structures). In such "multiple stage" machines the additional tables and/or support structures may be used in parallel, or preparatory steps may be carried out on one or more tables and/or support structures while one or more other tables and/or support structures are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if required, may be referred to as a radiation system.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
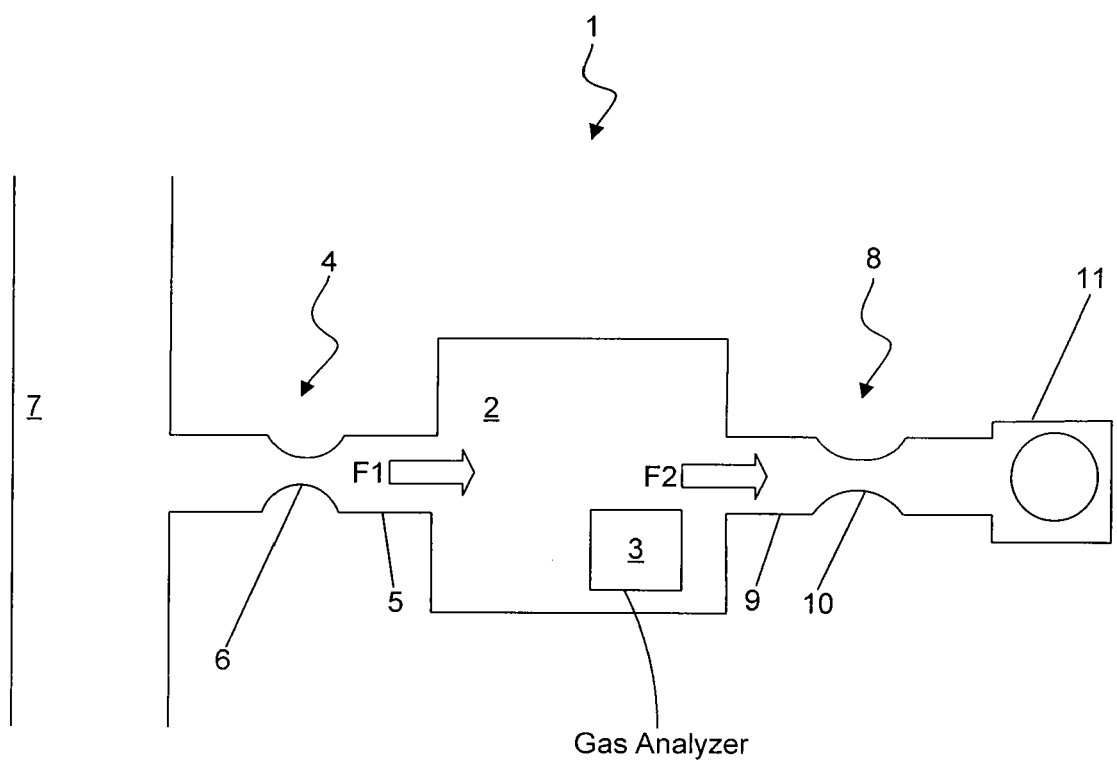
FIG. 2 depicts a schematic view of a gas analyzing system according to an embodiment of the invention.

FIG. 2 shows a schematic view of a gas analyzing system 1 according to an embodiment of the invention, which may be included in, for example, the lithographic apparatus described above. The system 1 has a reduced pressure chamber 2 and a gas analyzer 3 arranged therein. The gas analyzer 3 is implemented as a RGA, but another or alternative gas analyzer could be applied, e.g. a measurement system that might accomplish quantitative measurements. For proper functioning of the RGA, an extreme low pressure is present in the chamber 2 during operation of the system 1. As an example, the pressure inside the chamber 2 is in the order of $10^{-5}$ mbar. However, other pressure values may apply.

The chamber 2 may be provided with an inlet configuration 4 that is connected to an inlet channel section 5 having a restriction 6. The restriction 6 forms an orifice in a flow path towards the chamber 2. The inlet channel section 5 is connected upstream to a process chamber 7 in which the gas mixture to be analyzed is present. During operation, the pressure in the process chamber 7 is higher than in the reduced pressure chamber 2. As an example, the pressure in the process chamber 7 may be in the order of $10^{-1}$ mbar. Again, other pressure values may apply. In the process chamber 7, one or more optical components of, for example, the illumination system are arranged, the illumination system being included in the lithographic apparatus depicted in FIG. 1.

The restriction 6 in the inlet channel section 5 is designed such that, depending on the pressure in the process chamber 7, a desired pressure in the reduced pressure chamber 2 is obtained, e.g. for optimally exploiting a dynamic range of the RGA. For example, the restriction has a diameter in the order of approximately 100 microns to approximately 200 microns. During operation, a gas mixture inflow F1 flows via the inlet channel section 5 and the restriction 6 into the reduced pressure chamber 2.

Further, the reduced pressure chamber 2 is provided with an outlet configuration 8 for a gas mixture outflow F2. In this embodiment, a pump system 11 is connected downstream to the outlet configuration 8 to facilitate the gas mixture outflow. The outlet configuration 8 comprises a channel section 9 and a flow section 10. The cross-sectional area of the flow section 10 is smaller than the cross-sectional area of the channel section 9. The flow section is formed as an orifice, also called a restriction, that has a cross-sectional area optimized such that, for a main gas component in the gas mixture, the outflow resistance, seen from the reduced pressure chamber 2, is low.

By introducing the flow section 10 having a cross-sectional area that is smaller than the cross-sectional area of the channel section 9, particles having a smaller mass flow more easily through the flow section than particles having a larger mass. The poor performance of the pump for low particle mass gas is thus counteracted in such a way that the effective pumping speed for low particle mass gas (such as $H_2$) is larger than for the species of interest. As a result, a removal rate of low particle mass gas (such as $H_2$) is higher than a removal rate of the species of interest. Therefore, the partial pressure of the species of interest becomes higher and the contamination particles are better detectable by the gas analyzer. By calibrating the system properly for the mass transfer through the system, the mass spectrum can be calculated back to the original spectrum.

In a lithographic system application, the higher sensitivity of the gas analyzing system enables contaminants to be detected in an earlier stage of a lithographic process, so that the process can be stopped, if necessary, thus preventing possible damage of optics or sensors in the lithographic system.

As shown in FIG. 2, the flow section 10 is formed as an intermediate section of the channel section 9 having converging and diverging walls so that in a flow direction, the cross-sectional area subsequently, optionally gradually, decreases and increases. However, the flow section 10 might also be constructed otherwise, e.g. as a plate traversing and/or located transverse with respect to the orientation of the channel section 9 and provided with an aperture or the channel section 9 itself may be narrow. The flow section 10 may be located in an intermediate section of the channel section 9 or at an end of the channel section 9, such as near the reduced pressure chamber 2 or near the pump system 11. In particular, the flow section 10 may be provided in the wall of the reduced pressure chamber 2 so that the outflow F2 is realized from the reduced pressure chamber 2 through the flow section 10 into the channel section 9.

In an embodiment, the dimensions of the flow section 10 are chosen such that its form is substantially circular having a minimum diameter substantially between approximately 10 millimeters (±80 mm² area) and approximately 50 millimeters (±2000 mm² area). Desirably, the minimum diameter is substantially between approximately 20 millimeters (±310 mm² area) and approximately 40 millimeters (±1300 mm² area). In a practical example, the minimum diameter is approximately 28 millimeters (±620 mm² area).

During operation of the gas analyzing system, a diluted gas mixture flows from the process chamber 7 via the inlet configuration 4 to the reduced pressure chamber 2 for measurement. Then, the gas mixture flows via the outlet configuration 8 towards the pump system 11, also called a turbomolecular vacuum pump.

Figure 3:
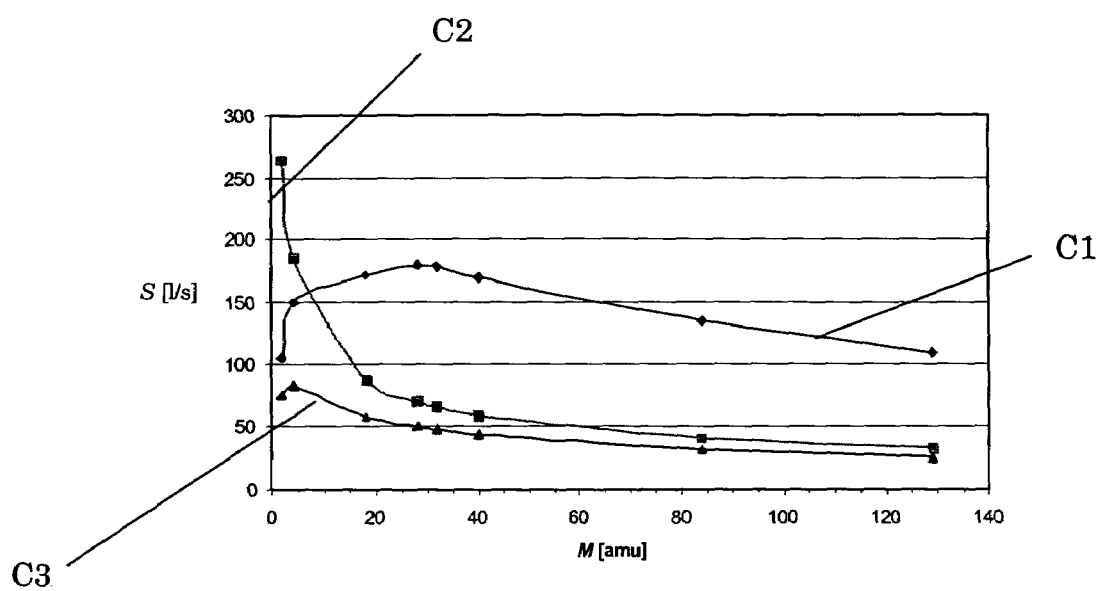
FIG. 3 depicts a graph with curves relating to physical characteristics of the gas analyzing system of FIG. 2.

The pump speed of a turbomolecular vacuum pump is dependent on the mass of the pumped gas. Most turbomolecular pumps have been optimized for pumping air ($N_2$ and/or $O_2$ having molecular mass 28 and 32, respectively) and water ($H_2O$ having molecular mass 18) and exhibit a lower pumping speed for lower mass (He and $H_2$) or higher mass (Kr, Ex, etc) gases. FIG. 3 shows a graph with simulated, calculated and/or empirical curves relating to the physical characteristics of the gas analyzing system, wherein a first curve C1 shows, as a function of the mass M of the gas particles in atomic mass units [amu], the described behavior of a Pfeiffer TMU200 pump having a nominal pump speed of 200 l/s.

For an orifice or other possible obstruction, the conductance for a particular gas, being the inverse of the flow resistance, is dependent on the square root of the inverse of the molecular mass of the flowing gas particles. In particular, in case of a circular hole, the formula for the conductance would be:

$$C = \frac{1}{8}\sqrt{\frac{2\pi RT}{M}}\, d^2,$$

wherein R denotes the universal gas constant, T denotes the absolute temperature [K], M denotes the molecular mass of the flowing particles [kg/mol] and d denotes the diameter of the circular hole [m]. The conductance behavior as a function of the molecular mass of the flowing particles is shown as a further curve C2 in FIG. 3.

For a specified outflow conductance and a pump arranged in series, the effective pump speed for a particular gas is given by $$\frac{1}{S_{\mathit{eff}}} = \frac{1}{C} + \frac{1}{S_{pump}},$$

wherein $S_{\mathit{eff}}$ denotes the effective pumping speed [l/s], C denotes the outflow conductance [l/s] and $S_{pump}$ denotes the pump speed of the pump [l/s].

The effective pump speed as a function of the molecular mass of the flowing particles is shown in FIG. 3 as a further curve C3. As can be seen the effective pumping speed is maximal for hydrogen gas particles (i.e., low molecular mass gas), thereby obtaining a relatively large removal of hydrogen compared to other gases, such as contaminant gas particles. As the partial pressures of contaminant gas particles are relatively high, a relatively high sensitivity of the gas analyzing system can be obtained.

In an embodiment, depending on the flow characteristics of the pump system, the cross-sectional area of the flow section may be optimized such that, for a main gas component in the gas mixture, the outflow resistance is low. As a consequence, the partial pressure of the main gas component may be minimized, so that the partial pressure of the species of interest becomes higher, thereby further improving the sensitivity of the gas analyzing system.

By enlarging an inflow resistance of the inlet configuration 4, the inflow of the gas mixture may be advantageously enlarged to counteract the reduced effective pumping speed caused by the flow section 10 of the outlet configuration 8. As a result, a desired pressure in the reduced pressure chamber may substantially be maintained, thereby also exploiting the dynamic range of the gas analyzer. Alternatively or additionally, a pump having a larger capacity may be applied.

The invention is not restricted to the embodiments described herein. It will be understood that many variants are possible. For example, instead of using a RGA, an alternative measurement device may be employed, such as an ionization mass spectrometer. Further, the dimensions of the cross-sectional area of the flow section may be optimized for any main gas component in the gas mixture, e.g. $N_2$, such that the outflow resistance is low.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. A method of analyzing a gas in a gas analyzing system, comprising a gas analyzer and a reduced pressure chamber within which is located the gas analyzer, the reduced pressure chamber having an inlet configuration for a gas mixture inflow and an outlet configuration for a gas mixture outflow, wherein the outlet configuration is connected to a pump system to facilitate the gas mixture outflow, the outlet configuration comprising a channel section, the method comprising:

providing the outlet configuration with a flow section that increases the resistance of gas flow for larger mass particles by having a cross-sectional area that is smaller than a cross-sectional area of the channel section;

increasing a partial pressure of a gas species of interest by decreasing a concentration of a main gas component of the gas mixture which has smaller mass particles and lower resistance through the flow section; and detecting the gas species of interest at increased partial pressures.

2. The method of claim 1, further comprising enlarging an inflow resistance of the inlet configuration.

3. The method of claim 1, further comprising enlarging a pump capacity of the pump system.

4. The method of claim 1, wherein the flow section is formed as an orifice.

5. The method of claim 1, wherein, depending on flow characteristics of the pump system, the flow section has a cross-sectional area such that, for a main gas component which has low particle mass in the gas mixture relative to other gases in the gas mixture, the outflow resistance is lower than for the other gases in the gas mixture.

6. The method of claim 1, wherein the flow section is substantially circular.

7. The method of claim 1, further comprising:
calibrating the system such that the level of each detected gas can be used to determine the original levels.

* * * * *